United States Patent
Akassoglou et al.

(10) Patent No.: US 9,669,112 B2
(45) Date of Patent: Jun. 6, 2017

(54) ANIMAL MODEL OF NEURONAL INJURY

(71) Applicant: The J. David Gladstone Institutes, San Francisco, CA (US)

(72) Inventors: Katerina Akassoglou, San Francisco, CA (US); Jae Kyu Ryu, San Francisco, CA (US)

(73) Assignee: THE J. DAVID GLADSTONE INSTITUTES, San Francisco, CA (US), A TESTAMENTARY TRUST ESTABLISHED UNDER THE WILL OF J. DAVID GLADSTONE ( * ) Notice: Subject to any disclaimer, the term of this patent is extended or adjusted under 35 U.S.C. 154(b) by 0 days.

(21) Appl. No.: 14/646,429

(22) PCT Filed: Nov. 20, 2013

(86) PCT No.: PCT/US2013/070900
§ 371 (c)(1),
(2) Date: May 21, 2015

(87) PCT Pub. No.: WO2014/081764
PCT Pub. Date: May 30, 2014

(65) Prior Publication Data
US 2015/0297754 A1     Oct. 22, 2015

Related U.S. Application Data

(60) Provisional application No. 61/728,904, filed on Nov. 21, 2012, provisional application No. 61/730,835, filed on Nov. 28, 2012.

(51) Int. Cl.
*A01K 67/00* (2006.01)
*A61K 49/00* (2006.01)
*C07K 14/75* (2006.01)
*A01K 67/027* (2006.01)

(52) U.S. Cl.
CPC ........ *A61K 49/0008* (2013.01); *A01K 67/027* (2013.01); *C07K 14/75* (2013.01); *A01K 2207/10* (2013.01); *A01K 2227/105* (2013.01); *A01K 2267/035* (2013.01); *A01K 2267/0318* (2013.01)

(58) Field of Classification Search
None
See application file for complete search history.

(56) References Cited

PUBLICATIONS

Schachtrup et al. J Neurosci 2010;30:5843-54.*
Masuda et al. Peptides 2002;23:409-11.*
Molendijk et al. Psychoneuronendocrinol 2015;62:389-91.*
Cortes-Canteli et al. Neuron 2010;66:695-709.*

* cited by examiner

*Primary Examiner* — Janice Li
(74) *Attorney, Agent, or Firm* — Convergent Law Group LLP

(57) ABSTRACT

The present invention provides non-human animal models of neuronal injury and/or cognitive dysfunction and methods of making and using such animal models. The animal models of the invention are particularly suited to assessing neurodegeneration in selected regions of interest in the CNS, and thus especially useful for testing the therapeutic efficacy of agents targeting neurodegeneration associated with aging, neurodegenerative diseases, autoimmunity and trauma (e.g., ischemia).

21 Claims, 9 Drawing Sheets

ANIMAL MODEL OF NEURONAL INJURY

CROSS-REFERENCE TO RELATED APPLICATIONS

This application claims the benefit of U.S. Provisional Patent Application Ser. No. 61/728,904, filed Nov. 21, 2012, and U.S. Provisional Patent Application Ser. No. 61/730,835, filed Nov. 28, 2012, both incorporated herein by reference.

GOVERNMENT SUPPORT

This invention was made with government support under Grant NS052189 awarded by the National Institutes of Health. The government may retain certain rights in the invention.

FIELD OF THE INVENTION

The present invention relates to the field of animal models of neuronal injury.

BACKGROUND OF THE INVENTION

In the following discussion certain articles and methods will be described for background and introductory purposes. Nothing contained herein is to be construed as an admission of prior art. Applicant expressly reserves the right to demonstrate, where appropriate, that the articles and methods referenced herein do not constitute prior art under the applicable statutory provisions.

Animal models of neurodegenerative disease are excellent tools for studying pathogenesis and therapies including cellular transplantation. Conventionally, there are two approaches to the development of animal models of neurodegenerative disease based on the etiology of the disease. These consist of genetically reproducing the mutations seen in inherited forms of neurodegeneration in animal models, and exposing animals to putative environmental toxins which mimic the clinical manifestations of the disease.

Both of these approaches have drawbacks, however, as neither is representative of the underlying physiological mechanisms for the actual induction of neuronal injury. As neurodegeneration is a multi-faceted event, the presence of a single genetic alteration is rarely enough to mimic the disease, and the exhibition of the neuronal defects may take quite a while, limiting the usefulness of the animal model. With toxins, the onset of the neurodegeneration is usually much quicker, but they often have unwanted (and usually unrelated) side effects that limit their usefulness.

There is thus a need in the art for new, physiologically relevant models of neuronal injury.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides non-human animal models of neuronal injury and/or cognitive dysfunction and methods of making and using such animal models. This includes non-human animal models of neurodegeneration, encephalomyelitis, and spinal cord injury. The animal models of the invention are particularly suited to assessing neuronal injury, e.g., neurodegeneration in selected regions of interest in the brain, and thus especially useful for testing the therapeutic efficacy of test agents, e.g., agents targeting neurodegeneration associated with aging, neurodegenerative diseases, autoimmunity and trauma (e.g., ischemia).

In one aspect, the invention comprises the introduction of a fibrinogen agent to a region of interest in a non-human animal to induce neuronal injury in that region of interest. Preferably the region of interest is in the central nervous system (CNS).

In another aspect, the invention comprises introduction of an agent that induces microglial activation to a region of interest in a non-human animal to induce neuronal injury in that region of interest. The non-human animals of the invention are useful in the identification of agents that inhibit neuronal injury, including neurodegeneration processes in the brain and/or spinal cord.

In a first embodiment, the invention provides a method of inducing neuronal injury in a region of interest in a non-human animal comprising the introduction of a fibrinogen agent to the region of interest.

Preferably, the introduction comprises local delivery of the fibrinogen agent to the region of interest, although the agent can also be delivered systemically. The introduction can also be targeted to a specific region of interest, e.g., through direct injection to the region of interest.

Alternatively, the fibrinogen agent can be delivered to multiple areas of interest, e.g., delivered to multiple regions in the brain though CNS infusion using local infusion or an osmotic pump.

In a specific aspect, the fibrinogen agent is full-length fibrinogen. In another aspect, the fibrinogen agent is a biologically active fragment of fibrinogen. In certain aspects the fibrinogen agent is labeled.

The invention also provides a method of inducing neuronal injury in a region of interest in a non-human animal comprising the introduction of an agent that induces microglial activation to the region of interest.

Preferably, the introduction comprises local delivery of an agent that induces microglial activation to the region of interest, although the agent can also be delivered systemically. The introduction can also be targeted to a specific region of interest, e.g., through direct injection to the region of interest.

Alternatively, the agent that induces microglial activation can be delivered to multiple areas of interest, e.g., delivered to multiple regions in the brain though CNS infusion using local infusion or an osmotic pump.

Regions of particular interest include, but are not limited to, the dentate gyrus, the substantia nigra, the corpus callosum, and the cortex. Other regions of interest in the CNS include the spinal cord.

In specific aspects, the agent that induces microglial activation is fibrinogen or a biologically active fragment thereof.

In specific aspects, the invention provides a method of inducing neuronal injury in one or more regions of interest in a non-human animal comprising the introduction of a composition comprising a fibrinogen agent to the one or more regions of interest.

In other specific aspects, the invention provides a method of inducing neuronal injury in one or more regions of interest in a non-human animal comprising the introduction of a composition comprising an agent that induces microglial activation to the one or more regions of interest.

In some aspects, the invention provides the use of a non-human animal model to study neuronal injury and/or cognitive dysfunction, wherein said neuronal injury in the non-human animal model is induced by the introduction of a composition comprising a fibrinogen agent to one or more regions of interest in a non-human animal, and wherein the non-human animal model exhibits neuronal injury and/or cognitive dysfunction.

In yet other specific aspects, the invention provides the use of a non-human animal model to study neuronal injury and/or cognitive dysfunction, wherein said neuronal injury in the non-human animal model is induced by the introduction of a composition comprising an agent that induces microglial activation to one or more regions of interest in a non-human animal, and wherein the non-human animal model exhibits neuronal injury and/or cognitive dysfunction.

The invention also provides a non-human animal comprising neuronal injury in a physiological region of interest, wherein said neuronal injury is induced by the introduction of a fibrinogen agent to the physiological region of interest.

The invention also provides a non-human animal comprising neuronal injury in a physiological region of interest, wherein said neuronal injury is induced by the introduction of an agent that induces microglial activation to the physiological region of interest.

More specifically, the invention provides a non-human model of neuronal injury and/or cognitive dysfunction generated by introducing a composition comprising a fibrinogen agent to one or more regions of interest in a non-human mammal, assessing neuronal function and/or cognitive function in the non-human mammal and selecting non-human mammals with impairment of neuronal function and/or cognitive function.

The invention also provides a non-human model of neuronal injury and/or cognitive dysfunction generated by introducing an agent that inhibits fibrinogen activity to one or more regions of interest in a non-human mammal, assessing neuronal function and/or cognitive function in the non-human mammal, and selecting non-human mammals with impairment of neuronal function and/or cognitive function.

Preferably, the non-human animals of the invention comprise neuronal injury in one or more regions of the CNS. In some aspects, the region of interest is in the brain, and the non-human animals exhibit cognitive impairment resulting from neurodegeneration. In some aspects, the region of interest is in the brain, and the nonhuman animals exhibit encephalomyelitis from demyelination. In other aspects, the region of interest is the spinal cord.

It certain aspects, the non-human animal is a wild-type animal. In other aspects, the animal further comprises one or more genetic traits associated with an increased risk of neurodegenerative disease, e.g., a transgenic animal comprising a mutation associated with a particular neurodegenerative disease. In yet other aspects, the animal model further comprises one or more genetic traits associated with a decreased risk of neurodegenerative disease. In still other aspects, the animal model further comprises one or more genetic traits associated with increased risk of demyelination. In yet other aspects, the animal comprises a genetic trait associated with absorption, distribution, metabolism and excretion of pharmacologic agents.

In another aspect, the invention provides a method for identifying inhibitors of neuronal injury, the method comprising: administering a test agent to a non-human animal and determining whether the test agent inhibits or reduces the ability of a fibrinogen agent to induce neuronal damage in the non-human animal host.

In yet another aspect, the invention provides a method for identifying inhibitors of microglial activation, said method comprising administering a test agent to a nonhuman animal and determining whether the test agent inhibits or reduces the ability of a fibrinogen agent to induce microglial activation in the region of administration of the test agent.

In still another aspect, the invention provides a method for identifying inhibitors of neurodegeneration, said method comprising administering a test agent to a nonhuman animal, and determining whether the test agent inhibits or reduces the ability of a fibrinogen agent to induce neurodegeneration in the region of administration of the test agent.

In yet another aspect, the invention provides a method for identifying inhibitors of encephalomyelitis, said method comprising administering a test agent to a nonhuman animal, and determining whether the test agent inhibits or reduces the ability of a fibrinogen agent to induce encephalomyelitis in the region of administration of the test agent.

In specific aspects, the invention provides a screening method for identification of an agent for the treatment of neuronal injury and/or cognitive dysfunction comprising introducing a composition comprising an agent that induces microglial activation to a physiological region of interest in a non-human mammal, administering a test agent to the non-human model, measuring cognitive and/or neuronal function in the non-human model following administration of the test agent, and comparing the cognitive and/or neuronal function of the non-human model to which the test agent has been administered to a control group not treated with test agent, and identifying the test agent demonstrated to ameliorate cognitive and/or neuronal function in the non-human model to which the test agent has been administered.

In other specific aspects, the invention provides a screening method for identification of an agent for the treatment of neuronal injury and/or cognitive dysfunction comprising introducing a composition comprising a fibrinogen agent to a physiological region of interest in a non-human mammal, administering a test agent to the non-human model, measuring cognitive and/or neuronal function in the non-human model following administration of the test agent, comparing the cognitive and/or neuronal function of the non-human model to which the test agent has been administered to a control group not treated with test agent, and identifying the test agent demonstrated to ameliorate cognitive and/or neuronal function in the non-human model to which the test agent has been administered.

In these specific aspects, the test agent can be administered prior to the introduction of the composition to the physiological region of interest. Alternatively, the test agent is administered following to the introduction of composition to the physiological region of interest.

In preferred aspects, the non-human animal model is a non-human mammalian model. In more specific aspects, the non-human animal model is a rodent, e.g., a mouse or a rat. In another specific aspect the non-human animal model is a non-human primate.

It is a feature of the invention that the methods of the invention surprisingly cause neuronal injury in various regions.

It is an advantage of the invention that the animal models can be easily created in various genetic backgrounds.

It is another advantage of the invention that the animal models do not require genetic manipulation to achieve the neuronal phenotypes of various disease states.

These and other aspects, features and advantages will be provided in more detail as described herein.

BRIEF DESCRIPTION OF THE DRAWINGS

FIG. 1A shows the time required for crossing in the Morris water maze, while FIG. 1B shows the amount of time spent in the specific quadrants of the maze for both control and fibrinogen-infused mice.

DETAILED DESCRIPTION OF THE INVENTION

Figures 1A, 1B:
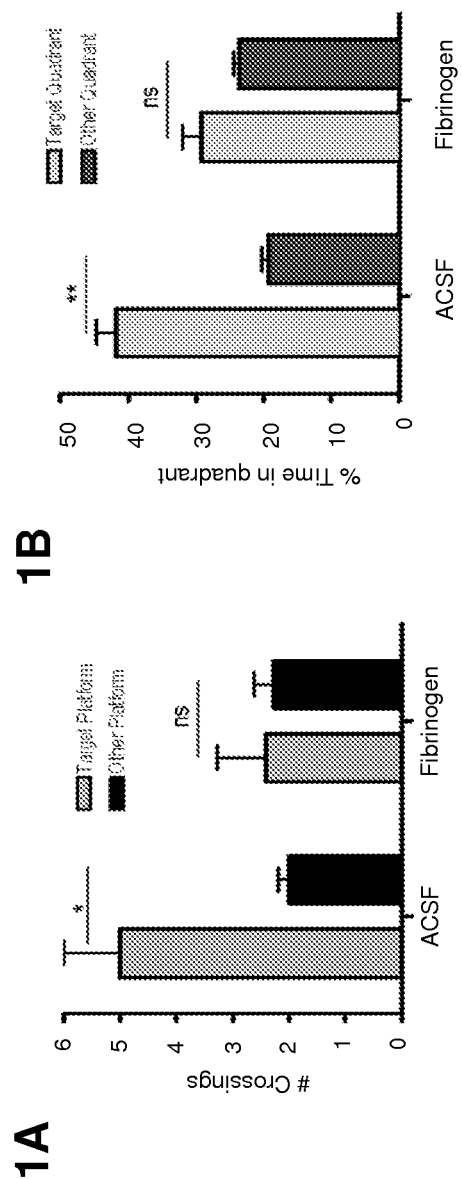
FIGS. 1A and 1B are bar graphs showing impaired memory recall exhibited by mice infused with fibrinogen.

The methods described herein may employ, unless otherwise indicated, conventional techniques and descriptions of molecular biology (including recombinant techniques), cell biology, biochemistry, and microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Harlow and Lane, Antibodies, A Laboratory Manual, Cold Spring Harbor Publications, New York, 1988; Sambrook and Russell, *Molecular Cloning: A Laboratory Manual* (2002) (all from Cold Spring Harbor Laboratory Press); Stryer, L., *Biochemistry* (4th Ed.) W.H. Freeman, New York (1995); Lehninger, *Principles of Biochemistry*, $3^{rd}$ Ed., W. H. Freeman Pub., New York (2000); and Berg et al., *Biochemistry*, $5^{th}$ Ed., W.H. Freeman Pub., New York (2002), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by appended claims.

It should be noted that as used herein and in the appended claims, the singular forms "a," "and," and "the" include plural referents unless the context clearly dictates otherwise. Thus, for example, reference to "an agent" refers to one, more than one, or mixtures of such agents, and reference to "a method" includes reference to equivalent steps and methods known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those included limits are also included in the invention.

All publications mentioned herein are incorporated by reference for the purpose of describing and disclosing the formulations and methodologies that are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Definitions

The term "animal" is used herein to include all vertebrate animals, except humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection or infection with recombinant virus. This introduced DNA molecule may be integrated within a chromosome, or it may be extrachromosomally replicating DNA.

The term "antibody" is intended to include any polypeptide chain-containing molecular structure with a specific shape that fits to and recognizes an epitope, where one or more non-covalent binding interactions stabilize the complex between the molecular structure and the epitope. As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Where bispecific antibodies are to be used, these may be conventional bispecific antibodies, which can be manufactured in a variety of ways (Bolliger and Winter, 1993), e.g., prepared chemically or from hybrid hybridomas, or may be any of the bispecific antibody fragments mentioned above. It may be preferable to use scFv dimers or diabodies rather than whole antibodies. Diabodies and scFv dimers can be constructed without an Fc region, using only variable domains, potentially reducing the effects of anti-idiotypic reaction. Other forms of bispecific antibodies include the single chain "Janusins" described in Traunecker et al, (1991). Such antibodies also include CRAbs, which are chelating antibodies which provide high affinity binding to an antigen, D. Neri, et al. J. Mol. Biol. 246, 367-373, and dual-variable domain antibodies as described in Wu C et al., Nat Biotechnol. 2007 November; 25(11):1290-7. Epub 2007 Oct. 14.

A "test agent" as used herein refers to any agent that is a candidate to treat a disease or symptom thereof.

A "fibrinogen agent" as used herein means any agent exhibiting all or partial activity of the full-length fibrinogen protein. Examples of fibrinogen agents that can be utilized in the animal models of the invention include, but are not restricted to: proteins, including derivatized or labeled fibrinogen or fragments thereof; active peptide fragments; antibodies or fragments thereof; small molecules; aptamers; peptidomimetics; and pharmacophores. In one specific aspect, the fibrinogen agent is the complete fibrinogen protein.

The term "encephalomyelitis" refers to a physiological state associated with neuronal injury due to loss of myelin. In specific aspects, it refers to a physiological state associated with myelin loss due to inflammation of the brain and/or spinal cord.

The term "microglial activation" as used herein can refer to processes associated with innate activation or adaptive activation of the microglia. Such activation may include morphological changes of the microglial cells, including shortening of cellular processes and enlargement of their soma, as well as the release of proinflammatory cytokines and chemokines, reactive oxygen and/or nitrogen intermediates, proteinases and complement proteins, and upregulation of cell surface activation antigens.

The term "neurodegeneration" refers to a physiological state caused by neuronal injury associated with neuronal loss and/or damage. In specific aspects, neurodegeneration refers to neuronal injury resulting in impaired cognitive function.

The term "neuronal injury" as used herein refers to any damage or dysfunction exhibited by neurons, including but not limited to loss of myelin, dendrite retraction, dendritic spine density reduction, axonal damage and neuronal death.

The term "neuronal injury" as used herein refers to any damage or dysfunction exhibited by neurons, including but not limited to dendrite retraction, dendritic spine density reduction, axonal damage and neuronal death.

The term "pharmaceutically acceptable carrier" as used herein is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. The use of such media and agents is well known in the art. Except insofar as any conventional media or agent is incompatible with the agents provided herein, use thereof in the composition is contemplated.

The terms "peptide," "polypeptide," and "protein" are used interchangeably herein, and refer to a polymeric form of amino acids of any length, which can include coded and non-coded amino acids, chemically or biochemically modified, labeled or derivatized amino acids, and polypeptides having modified peptide backbones.

The term "peptidomimetic" as used herein refers to a protein-like chain designed to mimic a peptide. They typically arise from modification of an existing peptide in order to alter the molecule's properties. For example, they may arise from modifications to change a molecule's stability, biological activity, or bioavailability.

The term "pharmacophore" is used herein in an unconventional manner. Although the term conventionally means a geometric and/or chemical description of a class or collection of compounds, as used here the term means a compound that has a specific biochemical activity or binding property conferred by the 3-dimensional physical shape of the compound and the electrochemical properties of the atoms making up the compound. Thus, as used here the term "pharmacophore" is a compound and not a description of a collection of compounds which have defined characteristics. Specifically, a "pharmacophore" is a compound with those characteristics.

The term "research tool" as used herein refers to use of any animal model or assay of the invention for scientific enquiry, whether academic or commercial in nature, including the identification and development of candidate therapeutic agents. The research tools of the invention are not themselves intended to be therapeutic or to be subject to regulatory approval; rather, the research tools of the invention are intended to facilitate research and aid in such development activities, including any activities performed with the intention to produce information to support a regulatory submission.

The term "small molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in an animal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The term "wild-type" refers to a gene, protein, and/or animal (e.g., mouse) that has the characteristics of that gene, protein, and/or animal when isolated from a naturally occurring source. A wild-type gene, protein, and/or animal is that which is most frequently observed in a population and is thus arbitrarily designated the "normal" or "wild-type" form of that molecule. In contrast, the term "modified" or "mutant" refers to a nucleic acid, protein, and/or animal that displays modifications in sequence and/or functional properties (i.e., altered characteristics) when compared to the wild-type nucleic acid, protein, and/or animal.

The Invention in General

The animal models of the present invention are based on the surprising determination by inventors that introduced fibrinogen agents and/or agents that activate microglia are able to cause neuronal damage and death in otherwise normal non-human animals. In particular, the inventors demonstrated that: 1) exposure of a tissue to a single agent could cause a robust and reproducible neuronal injury in that tissue, despite the numerous complex physiological activities known to be involved with neuronal injury and 2) a single agent has the ability to cause neuronal injury in various regions of interest within the CNS. The injury produced was shown to vary depending upon the particular tissue exposed to the agent, resulting in neuronal injuries that paralleled those seen in various human pathologies. This makes the animal models of the invention particularly useful in the study of various neurological disorders or injury, and the identification and optimization of therapeutic agents that can be used to treat such neurological disorders or injury.

Although high plasma levels of fibrinogen are linked to the onset of dementia and increase the risk of AD (Xu G et al. *Int J Clin Pract* 62(7): 1070-1075; van Oijen M et al., *Stroke* 36(12): 2637-2641.), prior to the invention described herein it could not have been predicted that the introduction of a single agent could have such a profound effect on neuronal activity and survival in multiple regions of the CNS.

The invention is largely based on the demonstration that stereotactic injection of fibrinogen into the regions of the mammalian CNS impact on neuronal activity and cause physiological responses including reduction of memory recall, neuronal loss, dendrite retraction and dendritic spine density reduction. The neurodegeneration demonstrated by the animal models of the invention induced by fibrinogen activity and/or microglial activation provide a pharmacodynamic model for rapid evaluation of therapeutic agents targeting neuron spine elimination and cognitive decline. The animal models of the invention are thus important research tools in developing treatments for cognitive decline in a variety of nervous system pathologies associated with blood brain barrier disruption, protein aggregation and vascular damage.

The animal models of the invention demonstrate numerous advantages over conventional transgenic or chemically-induced models of neurodegeneration. In contrast to most conventional animal models for neurodegenerative diseases that exhibit cognitive deficits, such as animal models for Alzheimer's disease (AD), which require genetic manipulation, breeding and maintenance, the animals of the present invention are advantageous over the conventional models of neurodegenerative disease as they can be created in a short period of time, allowing the animal models to be used (e.g., for testing of agents) within hours of creation of the model. For example, the neurodegenerative phenotype appears quite quickly following introduction of the agent, allowing the testing of test agents within 12 hours to 7 days as opposed to the three to nine months generally required for chronic genetic models to display a neurodegenerative phenotype. Moreover, rapid pharmacodynamics studies to directly compare the efficacy of central vs peripheral administration of compounds can be performed, which are not possible in chronic transgenic neurodegenerative models, where lesions are multifocal without predictable location.

In comparison with chemically-induced models of neuronal death, such as kainite or MPTP, the animal models of the invention are based on the introduction of an activity associated with a physiological plasma protein that is detected in the brain of human neurodegenerative diseases. In contrast to kainite, fibrinogen does not induce side effects not present in neurodegenerative diseases such as seizures, but instead induces memory deficits, which have direct clinical relevance to neurodegenerative diseases. And unlike chemical inducers such as methyl-4-phenyl-1,2,3,6-tetrahydropyridine (MPTP), which causes neuronal death in primates but not rodents, the effects of fibrinogen are conserved in mammalian species, allowing the creation of animal models of neurodegeneration in multiple species for use in drug development.

The neurodegeneration in the animal models of the invention occurs spontaneously, and thus does not require genetic manipulation or peripheral immunization. This allows the identification and optimization of test agents that directly affect the CNS effect of fibrinogen and/or microglial-associated neurodegeneration. As fibrinogen is associated with neurodegeneration and the activation of innate immune responses, the animal models allow studies of neuronal death, synaptic changes, and microglial activation in neurodegenerative diseases. Moreover, as the agents used in the animal models of the invention preferably spontaneously induce neurodegeneration without a peripheral immunization or genetic cross, they allow the testing of compounds to directly assess the effect in the CNS and not peripheral immune activation using adjuvants. This may be especially advantageous for testing anti-monocyte and anti-microglia drugs or drugs that target fibrinogen.

In addition, because the animal models are induced by introduction of an agent rather than genetic manipulation, they can easily comprise the genetic background of choice without the need for cross-breeding. The fibrinogen agent or microglial activator can thus be introduced into animals having mutations or polymorphisms in genes involved, e.g., in the neurodegenerative processes or in drug metabolism. Accordingly, an advantage of the animal models of the invention is the rapid assessment of drug efficacy in the genetic background of choice.

The animal models of the invention are believed to work through innate immune responses, allowing studies of neuronal death, synaptic changes, and microglial activation in various neurodegenerative diseases. This can be advantageous for testing various agents that are designed to modulate processes involved in neuronal injury.

The animal models of the invention are useful, e.g., to assess cognitive decline, memory deficits, neuronal loss and synaptic alterations. The animal models of the invention are especially useful as pharmacodynamic models to test the therapeutic efficacy of agents targeting neurodegeneration associated with aging, neurodegenerative diseases (e.g., arnyloidoses and tauopathies), autoimmunity (e.g., multiple sclerosis) and trauma (e.g., ischemia).

Compositions comprising a fibrinogen agent and/or an agent that induces microglial activation comprise the agent and a pharmaceutically acceptable carrier. The composition is formulated to be compatible with its intended route of administration. Suitable methods of administering such compositions include, but are not limited to, injections, sustained-release formulations, oral delivery, implant delivery systems, e.g., osmotic pump, and the like. Such delivery systems allow for the controlled and concentrated delivery of the compositions to a region of interest. The exact formulation employed will depend on the type of application that is desired and the nature of the fibrinogen agent. In certain aspects, the compositions are injected into the area of interest in the CNS.

Genetic Traits Associated with Neurodegenerative Disease and Drug Treatment

Although the models provided herein are generally described with wild-type animal hosts, the animal models of the invention are envisioned to encompass non-human animals with various genetic backgrounds, including but not limited to animals with genetic characteristics that may impact on the neurodegenerative process or activity of drugs that are intended to modulate the neurodegenerative process. Such animal models may include, but are not limited to transgenic animals with mutations associated with increased risk of neurodegeneration or animal models with genetic variation associated with neuroprotection.

Thus, in some aspects, the animal models of the invention also comprise genetic traits that are associated with an increased incidence of neurodegeneration or a neuroprotective trait. In certain preferred aspects, the animal models have genomes modified with mutations that are substantially similar to or mimic the mutations found in humans that have an increased prevalence of Alzheimer's disease, Parkinson's disease, multiple sclerosis, frontotemporal dementia, Pick disease, dementia pugilistica, corticobasal degeneration, genetic prion disorders, and progressive supranuclear palsy.

In certain aspects, the animal models comprise mutations in genes associated with enhanced protein aggregation. Exemplary genes associated with amyloidosis include huntingtin, associated with Huntington's disease; atrophin-1, ataxin 1-3 and the androgen receptor, which are associated with polyglutamine disease; apoE alleles, amyloid precursor protein, presenilin 1, 2, kinase D interacting substrate (Kidins220), glycogen synthase kinase 3-β (GSK3β) and protein phosphatase 1 (PP1), which are associated with Alzheimer's disease; tau, which is associated with frontotemporal dementia; α-synuclein (SNCA), leucine-rich repeat kinase 2 (LRRK2), UCHL-1, Parkin (PARK2), PTEN-induced putative kinase 1 (PINK1), DJ-1, vacuolar protein sorting 35 (VPS35), glucocerebrosidase gene (GBA) and ATP13A2, which are associated with Parkinson's disease; and superoxide dismutase, which is associated with amyotrophic lateral sclerosis. Chaperones also have a more general but critical role to suppress the appearance of misfolded species and to enhance protein folding, and thus animal models may comprise mutations in chaperones to increase levels of protein misfolding and thus protein aggregation.

In other aspects, the animal models comprise genetic traits associated with neuroprotective activity. Examples of such alterations include the apoE2 allele.

In some aspects, the animal models of the invention comprise genetic variations that affect absorption, distribution, metabolism and excretion ("ADME") of pharmacologic agents. The distribution of the common variant alleles of genes that encode drug metabolizing enzymes, drug transporters and drug targets has been found to vary among different populations. It thus can be advantageous to have animal models that reflect certain drug metabolic polymorphisms associated with ADME to assess the ability of agents to inhibit neuronal injury in different populations. Introducing variations in metabolizing enzymes, drug transporters and drug targets to the animal models of the invention can allow investigation of inter-individual variability in drug clearance and responses for treatment of neuronal injury.

For example, polymorphisms in the cytochrome P450 (CYP) family such as CYP2D6, CYP2C19 and CYP2C9 gene polymorphisms and gene duplications account for the most frequent variations in phase I metabolism of drugs since nearly 80% of drugs in use today are metabolized by these enzymes. Approximately 5% of Europeans and 1% of Asians lack CYP2D6 activity, and these individuals are known as poor metabolizers. CYP2C9 is another clinically significant drug metabolizing enzyme that demonstrates genetic variants. Studies into CYP2C9 polymorphism have highlighted the importance of the CYP2C9*2 and CYP2C9*3 alleles.

Extensive polymorphism also occurs in a majority of Phase II drug metabolizing enzymes. One of the most important polymorphisms is within the thiopurine S-methyltransferases (TPMT) that catalyze S-methylation of thiopurine drugs. With respect to drug transport polymorphism, the most extensively studied drug transporter is P-glycoprotein (P-gp/MDR1), but the current data on the clinical impact is limited. Polymorphisms in drug transporters may change a drug's distribution, excretion and response. Recent advances in molecular research have revealed that many of the genes that encode drug targets demonstrate genetic polymorphism. These variations, in many cases, have altered the target's sensitivity to the specific drug molecule and thus have a profound effect on drug efficacy and toxicity. For example, the beta (2)-adrenoreceptor, which is encoded by the ADRB2 gene, illustrates a clinically significant genetic variation in drug targets. The variable number tandem repeat polymorphisms in serotonin transporter (SERT/SLC6A4) gene are associated with response to certain classes of drugs.

Identification of Potential Therapeutic Agents Using Test Agents and the Animal Models of the Invention The animal models of the invention can also be used as research tools for the discovery and development of therapeutic products for modulation of a biological process involved in neuronal injury and cognitive disorders. The models may be useful in various aspects of drug discovery and investigation, including without limitation the initial identification of an agent as a drug candidate, the confirmation of activity of a drug candidate, and the identification of activity in an existing pharmaceutical product.

Test agents may be a protein, polypeptide, organic or inorganic molecule, carbohydrate, or other compound which may inhibit the fibrinogen activity and/or microglia activation. Such test agents include agents which are natural products or which are prepared synthetically. Non-limiting examples include polypeptides, peptidomimetics, pharmacophores, small molecules, the compounds found in the U.S. Pharmacopoeia, and the products of combinatorial chemical synthesis. Candidate pharmaceuticals include molecules for which no function is known, but which have structural similarity to known compounds with one or more known functions.

The test agent is administered to supply a desired therapeutic dose to promote a desired therapeutic response to the therapeutic area. By "desired therapeutic response" is intended an improvement in the condition or in the symptoms associated with the condition, including the inhibition of angiogenesis. The test agents can be formulated in a unit dosage such as a solution, suspension or emulsion, in association with a pharmaceutically acceptable carrier. Such carriers are inherently nontoxic and nontherapeutic. Examples of such carriers are saline, Ringer's solution, dextrose solution, and Hanks' solution. Nonaqueous carriers such as fixed oils and ethyl oleate may also be used. The vehicle may contain minor amounts of additives such as substances that enhance chemical stability, including buffers and preservatives.

Various methods of delivery can be used to deliver the test agent to the region of interest in the CNS, and will in part be dependent upon the agent and its bioavailability. For example, small molecules or other agents that are bioavailable may be administered orally, whereas protein-based agents are generally but not exclusively administered parenterally. Certain agents may be administered systemically, while others may be more beneficial with a local delivery. The method of delivery will be apparent to one skilled in the art upon reading the specification, and can be determined in view of the specific properties of the test agent.

A pharmaceutically effective amount of a test agent of the invention is administered to a subject. By "pharmaceutically effective amount" is intended an amount that is useful in the treatment of a disease or condition. In this manner, a pharmaceutically effective amount of the test agent can be introduced to the region of interest in a non-human animal model of the invention. By "therapeutically effective dose or amount" or "effective amount" is meant an amount of the test agent that, when administered, brings about a positive therapeutic response with respect to neuronal injury. In some embodiments of the invention, the therapeutically effective dose is in the range from about 0.1 µg/kg to about 100 mg/kg body weight, about 0.001 mg/kg to about 50 mg/kg, about 0.01 mg/kg to about 30 mg/kg, about 0.1 mg/kg to about 25 mg/kg, about 1 mg/kg to about 20 mg/kg, about 3 mg/kg to about 15 mg/kg, about 5 mg/kg to about 12 mg/kg, about 7 mg/kg to about 10 mg/kg or any range of value therein. It is recognized that the method of treatment may comprise a single administration of a therapeutically effective dose or multiple administrations of a therapeutically effective dose.

It is understood that the effective amount may vary depending on the nature of the effect desired, frequency of treatment, any concurrent treatment, the health, weight of the recipient, and the like. See, e.g., Berkow et al., eds., *Merck Manual*, 16th edition, Merck and Co., Rahway, N.J. (1992); Goodman et al., eds., *Goodman and Oilman's The Pharmacological Basis of Therapeutics*, 8th edition, Pergamon Press, Inc., Elmsford, N.Y. (1990); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston (1985), Katzung, *Basic and Clinical Phamacology*, Appleton and Lange, Norwalk, Conn. (1992), which references and references cited therein, are entirely incorporated herein by reference.

The test agent may be contained in a pharmaceutically-acceptable carrier, and supplementary active compounds can also be incorporated into the test agents. A composition comprising a test agent is formulated to be compatible with its intended route of administration. Examples of routes of administration include intravenous, intraarterial, intracoronary, parenteral, subcutaneous, subdermal, subcutaneous, intraperitoneal, intraventricular infusion, infusion catheter, balloon catheter, bolus injection, direct application to tissue surfaces during surgery, or other convenient routes. The composition can also be injected into an ischemic area of interest, to pharmacologically start the process of blood vessel growth and collateral artery formation.

Solutions or suspensions used for such administration can include other components such as sterile diluents like water for dilution, saline solutions, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The composition can be enclosed in ampoules, disposable syringes or multiple dose vials made of glass or plastic.

Compositions comprising test agents suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent possible. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms in the compositions can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin. Sterile injectable solutions can be prepared by incorporating an agent in the required amount in an appropriate solvent with a selected combination of ingredients, followed by filter sterilization. Generally, dispersions are prepared by incorporating an agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

1. In preferred aspects, the animals treated with a composition comprising a test agent are compared to a control group of animals not treated with test agent. Such a control group may be animals matched in physiological characteristics (e.g., age, strain, genetic background, etc.) that has not received the composition that comprises a test agent. In certain aspects, the control group not treated with the test agent receives no composition. In other aspects, the control group not treated with a test agent receives a composition with all or a subset of the elements used in the composition comprising the test agent except for the test agent itself. These control groups allow the identification of a physiologically significant effect of the control agent by comparison to matched animals that do not receive the control agent.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Induction of Cognitive Decline and Decreased Memory Recall by Chronic Lntracerebroventricular Infusion (ICV) of Fibrinogen to the CNS of a Mammal Fibrinogen was delivered to the central nervous system (CNS) of wild-type mice by ICV. Briefly, fibrinogen (5 mg/ml) or artificial cerebrospinal fluid (ACSF), a control, was infused into the CNS of the mice using 14-day Alzet pumps through a cannula implanted in the right lateral ventricle. The concentration of the fibrinogen solution was selected based on its physiological range in the plasma. Five days after pump implantation, the mice were trained in the Morris water maze and tested after removal of the target platform 24 hours after the last learning trial. Fibrinogen-infused mice had impaired memory recall, as exhibited by no difference in the number of crossings of the target platform (FIG. 1A) or time spent in the target quadrant (FIG. 1B) The ACSF-infused control mice crossed the target platform significantly more times and also spent significantly more time in the target quadrant. To control for visual discriminative ability, the same mice located a clearly visible black platform 2 h after the last trial. No changes were observed in swimming speed.

This demonstrated that an infusion of fibrinogen into the CNS of a mouse can induce cognitive decline and adversely impact memory recall.

Figure 2:
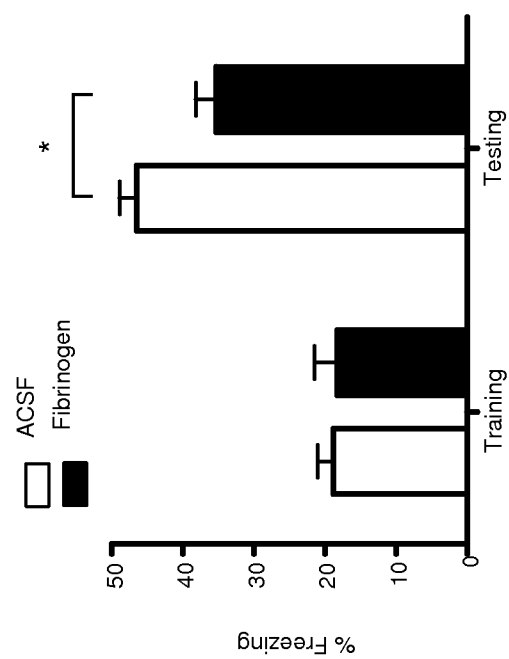
FIG. 2 is a graph showing impaired memory retrieval in the fear conditioning test 7 days after fibrinogen injection in the dentate gyrus of wild-type mice as compared to controls. * p<0.05, n=7-9.

Example 2: Induction of Neuronal Damage and Cognitive Decline by Injection of Fibrinogen in the Dentate Gyrus of a Mammalian Brain To assess the effect of an increase in the local concentration of fibrinogen in a specific region of interest in the brain, mice received a single stereotactic injection of either 5 µg fibrinogen (1 µl of 5 mg/ml fibrinogen) or 1 µl control (ACSF) in the dentate gyrus. The effects on memory retrieval were assessed in the contextual fear conditioning test (Riley C et al., (2012) Expert review of neurotherapeutics 12(3):323-333.). Mice were placed in a novel environment and given a brief foot shock (training day; day 6 post injection). Memory was assessed by placing the mice in the same environment again one day after the training day (testing day, day 7 post-injection) and freezing (anxiety) behavior was recorded. Percentage of freezing is a direct measure of memory retrieval. Fibrinogen injected animals presented a significant decrease in percentage of freezing, as illustrated in FIG. 2. These data indicate that a single, localized injection of fibrinogen in a first brain region of interest can cause memory impairment.

To assess the effects of fibrinogen injection on neurons in the dentate gyrus, mice mice received a single stereotactic injection of either 5 µg fibrinogen (1 µl of 5 mg/ml fibrinogen) or 1 µl control (ACSF) and neurodegeneration was examined in the hippocampus using labeled antibodies against NeuN as a neuronal marker (Sarnat H B et al., Brain and Development, Volume 20, Issue 2, March 1998, Pages 88-94) and labeled antibodies against IBA-1 as a marker of microglial activation (Ahmed Z et al., J Histochem Cytochem July 2007 vol. 55 no. 7, 687-700).

Figures 3A, 3B:
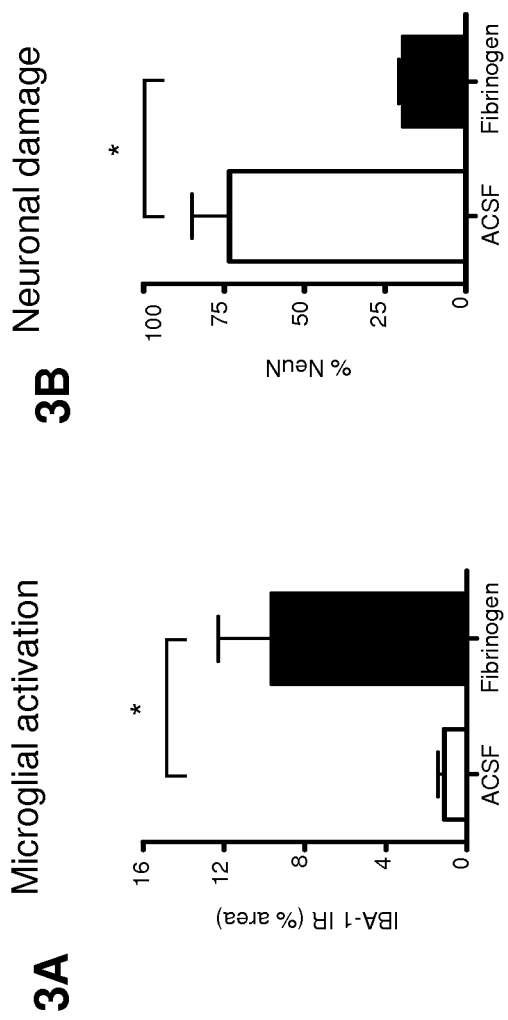
FIGS. 3A and 3B are bar graphs showing an increase in IBA-1 staining (FIG. 3A) and a reduction in NeuN staining (FIG. 3A) in mice who received an injection of fibrinogen in the hippocampus as compared to control ACSF injected mice.

At day 7 post injection, increased microglial activation was exhibited as evidenced by the IBA-1 antibody staining (FIG. 3A) of hippocampal tissue, while a dramatic decrease of NeuN immunoreactivity was observed, indicative of neuronal loss (FIG. 3B). These data indicate that a single injection of fibrinogen can cause neuronal loss and microglial activation in the hippocampus.

Figure 4:
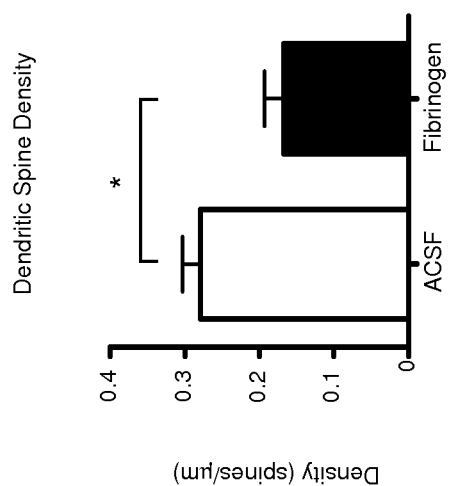
FIG. 4 is a bar graph showing quantification of reduced dendritic spine density when fibrinogen or ACSF is injected into the cortex. *p<0.05.

Example 3: Reduction of Dendritic Spine Density by Injection of Fibrinogen in the Cortex of a Mammalian Brain Fibrinogen injection in the cortex reduces dendritic spine density. Dendritic spines are the major site of excitatory synaptic inputs in the brain (Nimchinsky E A, et al., Annu Rev Physiol. 64:313-353). Novel spine formation and pre-existing spine elimination reflect the structural consequences of dynamic changes in neuronal activity at the cellular level (Grutzendler J & Gan W B (2006) NeuroRx 3(4):489-496; Trachtenberg J T et al., (2002) Nature 420 (6917):788-794; Grutzendler J et al. (2002) Nature 420 (6917):812-816.). Thus, dynamic changes in spine numbers and morphology are considered the cellular mechanisms underlying memory and learning (Holtmaat A et al. (2006) Nature 441 (7096):979-983). To assess the effect of a local concentration of fibrinogen on spine morphology, we injected fibrinogen by stereotactic injection into the cortex, and the brains were examined 3 days later by Golgi staining. Fibrinogen reduced the density of dendritic spines by 33%, compared to ACSF controls (FIG. 4). These data demonstrate that a single injection of fibrinogen is sufficient to induce rapid alterations in spine density.

In vivo 2P imaging to study the effect of fibrinogen on dendritic spines in the cortex of living mice. In vivo 2P microscopy reveals dynamic dendritic and spine alterations in response to fibrinogen. Thy1-YFP H mice expressing yellow fluorescent protein in a subpopulation of cortical neurons (Feng G et al. (2000) Neuron 28(1):41-51) were used, and baseline images were taken through a thinned skull as described (Grutzendler J, et al., (2002) Nature 420(6917):812-816; Aguilera T A et al. (2009) Integr Bioi (Cam b) 1 (5-6):371-381; Davalos D et al. (2005) Nat Neurosci 8(6):752-758. The mice then received a stereotactic injection of Alexa 594-labeled fibrinogen or ACSF using a Hamilton syringe, angled towards the cortex under the thinned skull. Three days post injection the mice were imaged for a second time, using the vasculature to identify the same area (Davalos D & Akassoglou K (2012) J Vis Exp (59):e2760; Davalos D et al., (2008) J Neurosci Methods 169(1):1-7). Fibrinogen caused extensive dendrite retraction 3 days after injection. In contrast, injection of a control protein such as Alexa594-labeled albumin did not alter dendritic structure (data not shown). At higher magnification, remaining dendrites show clearly defined spines at baseline, but not after fibrinogen injection, similar to Golgi stained sections. Together, these data demonstrate that an intracerebral injection of fibrinogen is sufficient to alter dendrite and spine morphology in the cortex.

Figures 5A, 5B:
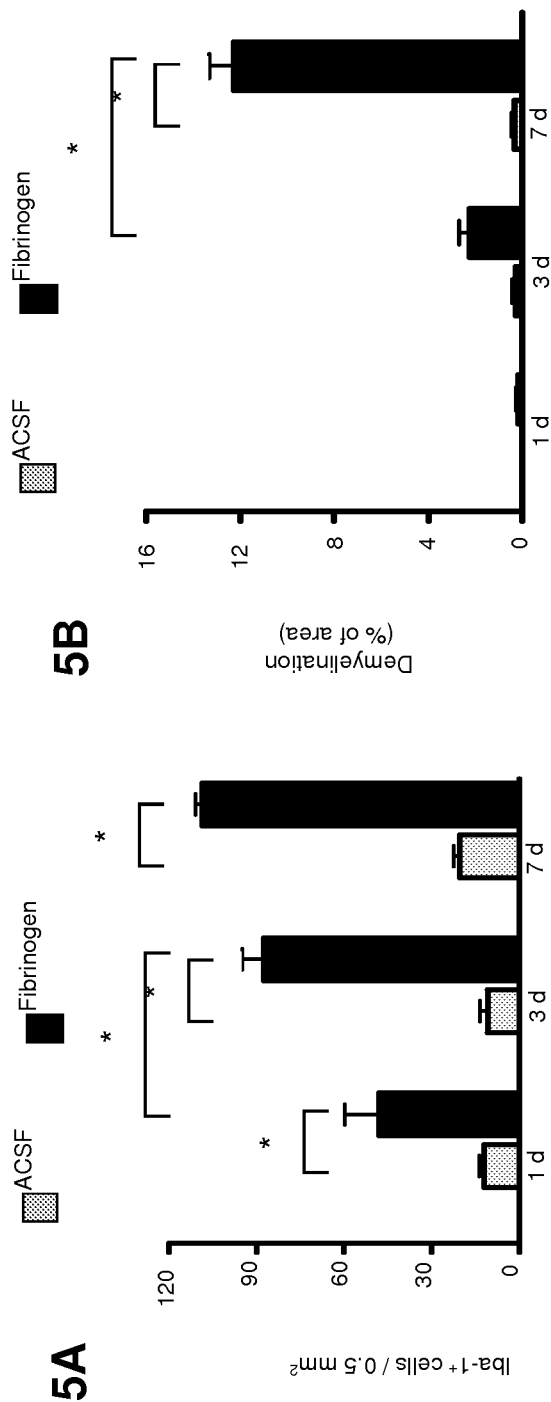
FIGS. 5A and 5B are bar graphs showing microglial activation and demyelination following fibrinogen injection in the corpus callosum. *p<0.05.

Example 4: Reduction of Myelination by Injection of Fibrinogen in the Corpus Callosum of a Mammalian Brain Fibrinogen was stereotactically injected at physiological concentrations into the corpus callosum. After 7 days, a single injection of fibrinogen was demonstrated to spontaneously induced demyelination in the corpus callosum. Fibrinogen induced primary demyelination with axonal sparing associated with microglia activation (MBP/IBA-1). Microglial activation was rapidly induced within 1 day after fibrinogen injection and preceded the appearance of demyelination (FIG. 5). Overall, these results suggest that fibrinogen is sufficient to trigger microglial activation, and subsequent inflammatory demyelination in the CNS in the absence of a pre-existing vascular, inflammatory or myelin abnormality.

Figures 6A, 6B:
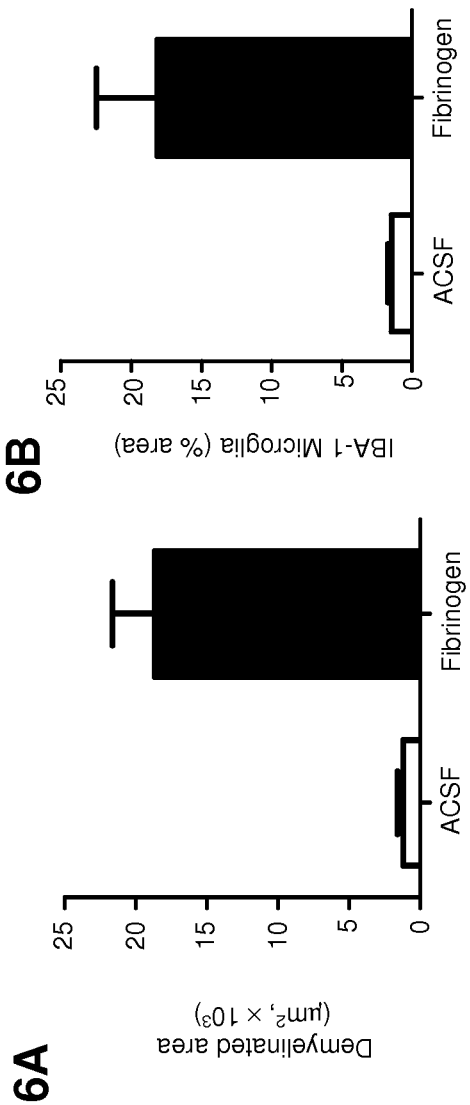
FIGS. 6A and 6B are bar graphs showing microglial activation and demyelination following fibrinogen injection in the spinal cord.

Example 5: Reduction of Myelination by Injection of Fibrinogen in the Spinal Cord Fibrinogen was also demonstrated to cause neuronal injury in the spinal cord, demonstrating that it demonstrates this activity in various tissues of the CNS. Either ACSF or fibrinogen was stereotactically injected at physiological concentrations into the spinal cord of wild-type mice (each Group n=3-4). After 7 days, a single injection of fibrinogen was demonstrated to have spontaneously induced demyelination and microglia activation in the spinal cord, as demonstrated by induced area of demyelination (FIG. 6A) and IBA-1 staining (FIG. 6B). The % area for IBA-1 staining indicates a percentage of the mean area of CD3 or IBA-1 immunoreactivity in the predefined area on spinal cord sections.

Overall, these results suggest that fibrinogen is sufficient to trigger microglial activation and inflammatory demyelination in the spinal cord as well as the brain of wildtype animals.

Example 6: Fibrinogen Induces Microglial Activation In Vivo

To directly address whether fibrinogen alone was sufficient to trigger acute microglial responses in the CNS, fibrinogen was injected into the cortex of Cx3cr1GFPI+ mice using a glass microelectrode. Control electrodes were also used containing ACSF or albumin (5 mg/ml). Injection of 5-10 µl of a 3-6 mg/ml fibrinogen solution, which approximates the physiological concentration of fibrinogen in plasma, caused rapid extension of microglial processes toward the tip of the electrode within ~30 minutes of the injection. The size of the fibrin deposit remains unaltered, and the microglial response to fibrin persists for at least 6 hours.

Figure 7:
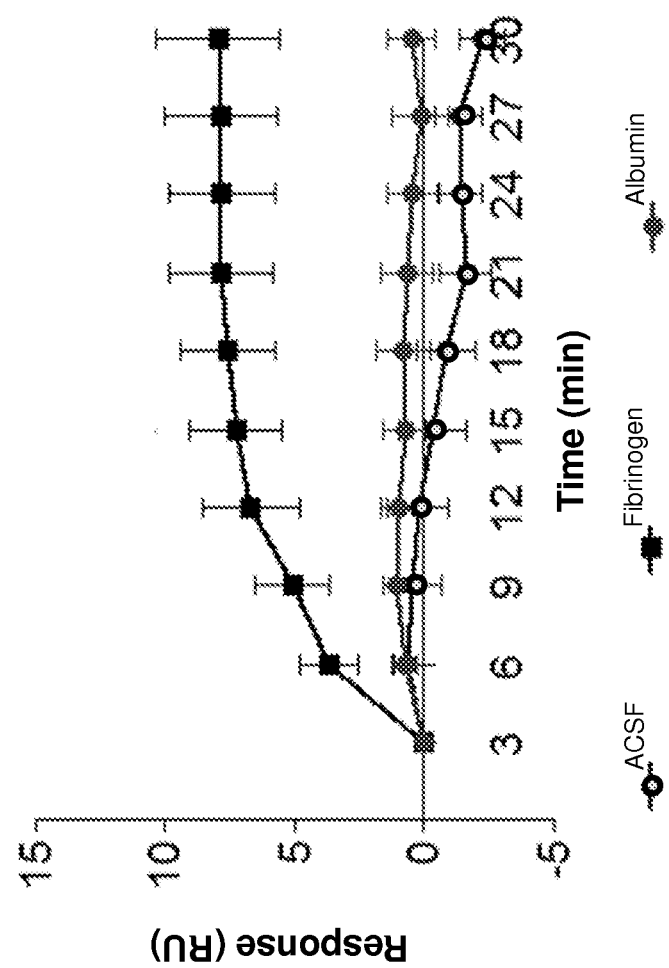
FIG. 7 is a graph illustrating the effects of local injection of fibrinogen (3-6 mg/ml) albumin or ACSF in the cortex of the Cx3cr1GFPI+ mice. Albumin and ACSF (n=7) and fibrinogen (n=9).

Quantification of microglia showed a robust and statistically significant increase of microglial responses to fibrinogen compared to the control injections of ACSF or the blood protein albumin (FIG. 7). The levels of microglia were quantified in vivo usingantibodies against IBA-1 (Ahmed Z, supra). Imaging of fibrin deposits over time showed that microglial clustering around fibrin was persistent at the injection site and microglia remained closely associated with fibrin for at least 6 hours.

Figure 8:
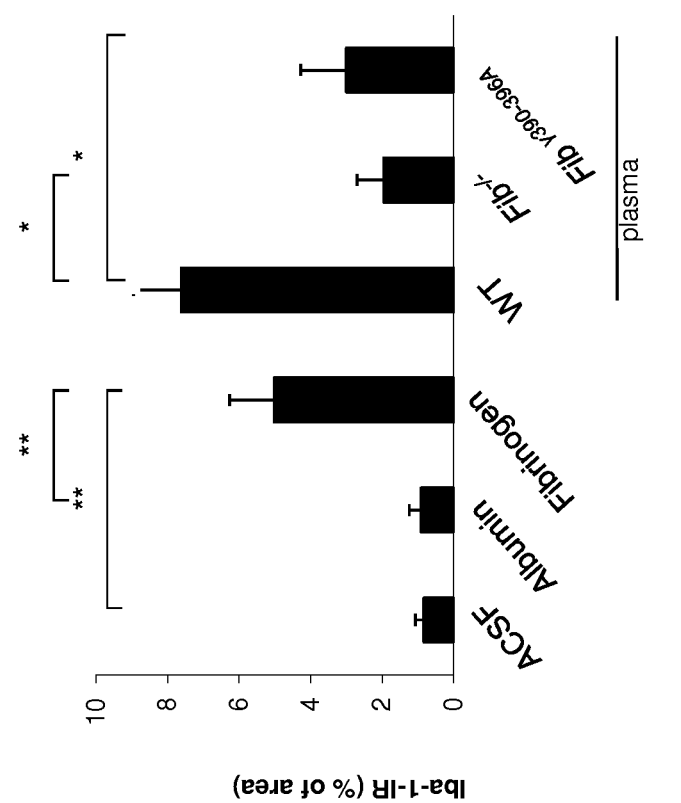
FIG. 8 is a bar graph illustrating the quantification of microglial immunoreactivity from mouse brain sections 3 days after stereotactic injections of fibrinogen, ACSF or albumin protein control, or plasma isolated from wt, Fib-I-, Fib_390-396A mice (n=6 mice per condition). The bar graph represents the mean (*P<0.05, **P<0.01, one-way ANOVA).

Since neuroinflammatory disease occurs over the course of days to weeks, the persistent fibrinogen-induced microglial activation was also examined over longer time periods. Higher concentrations of fibrinogen were introduced (6-10 mg/ml), as well as ACSF, albumin, or plasma isolated from wt, Fib-l-, Fib_390-396A mice (n=6 mice per condition). 3 days after stereotactic injections the fibrinogen injected at higher concentration (6-10 mg/ml) formed a deposit that is surrounded by microglial processes unlike the ACSF or albumin control (FIG. 8). Like fibrinogen, wildtype (WT) plasma induced microglial activation three days after injection. In contrast, microglial activation was markedly lower after injection of Fib-l-plasma containing virtually every plasma protein with the exception of fibrinogen. Similarly, injection of plasma isolated from fibrinogen Fib_390-396A knock-in mice, in which fibrinogen has been mutated to lack the CD11b/CD18 binding motif, yet it retains normal clotting function, showed a reduction of microglial activation (FIG. 8). Quantification showed significantly reduced microglial activation in response to Fib-l- or Fib_390-396A plasma compared to WT plasma. Overall, these results suggest that upon increased vascular permeability in the CNS fibrinogen is sufficient and specific among plasma proteins in triggering microglial responses. This also demonstrated that introduced fibrinogen can induce rapid and sustained microglial responses in vivo.

Example 7: Fibrinogen Activity in Mice with Different Genetic Backgrounds

Figures 9A, 9B:
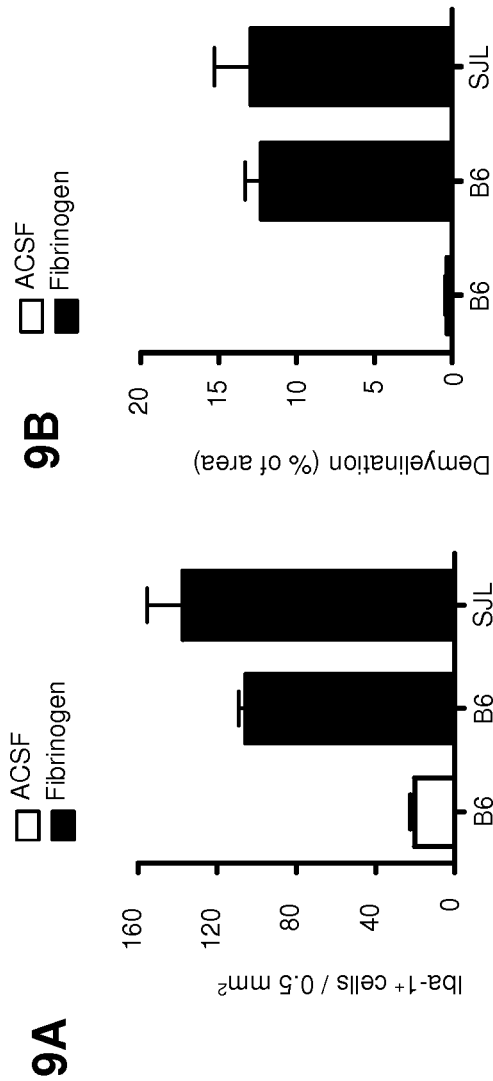
FIGS. 9A and 9B are bar graphs illustrating the effect of fibrinogen injection in different mice strains.

The experiment described in Example 4 was repeated using different mouse strains to investigate the possibility that the neuronal damage induced by fibrinogen was limited to mice with particular genetic backgrounds. As illustrated in FIGS. 9A and 9B, stereotactic injection of fibrinogen into the corpus callosum was able to cause significant demyelination and microglial activation in both C57BL/6 mice (B6) and SJL/J mice (SJL). This is particularly significant as in the traditional model for multiple sclerosis, experimental allergic encephalomyelitis (EAE), different strains of mice show varying degrees of susceptibility to EAE. EAE is a T cell-mediated autoimmune disease that can be induced in experimental animals by immunization with myelin antigens. The susceptibility to myelin antigens ranges from highly susceptible SJL/J mice to resistant B10.S mice. The fact that fibrinogen has induced a significant level of neuronal injury in all strains tested to date indicates that this model can be used in various genetic backgrounds, including backgrounds altered to have an increased susceptibility to neuronal injury or those that mimic human diseases or traits.

Example 8: Identification of Agents that Inhibit Fibrinogen-induced Neuronal Injury in the Corpus Callosum Test agents can be tested in the models of the invention to identify the ability of agents to prevent or decrease the activity of fibrinogen agents and/or microglial activation. Functional grade purified anti-CD11b antibodies (M1/70; eBioscience, San Diego, Calif.) or isotype control IgG (eBioscience, San Diego, Calif.) were injected (0.2 µl/min) with a 10-µl syringe attached to a 33-gauge needle into cerebral ventricle (AP, -2.0 mm; ML, 0 mm, DV, -2.0 mm) 30 min prior to stereotactic fibrinogen injection in the corpus callosum. Anti-CD11b inhibited T cell and monocyte infiltration, and reduced gene expression of CXCL10 and MCP-1.

The preceding merely illustrates the principles of the invention. It will be appreciated that those skilled in the art will be able to devise various arrangements and equivalents which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A non-human animal model of neuronal injury, wherein a fibrinogen agent is administered to one or more regions of the animal's central nervous system (CNS), and wherein said fibrinogen agent induces neuronal injury associated with microglial activation in the CNS.

2. The non-human animal of claim 1, wherein administration of a fibrinogen agent results in a decrease in dendritic spine density.

3. The non-human animal of claim 1, wherein the fibrinogen agent is administered to one or more regions of the brain.

4. The non-human animal model of claim 1, wherein the region of interest is the dentate gyrus, substantia nigra, cortex or corpus callosum.

5. The non-human animal of claim 1, wherein the animal exhibits cognitive impairment resulting from the neuronal injury.

6. The non-human animal of claim 1, wherein the fibrinogen agent is administered to the spinal cord.

7. The non-human animal of claim 1, wherein the induced neuronal injury is localized neuronal injury.

8. The non-human animal of claim 1, wherein the animal model further comprises one or more genetic traits associated with an increased risk of neurodegenerative disease.

9. The non-human animal model of claim 1, wherein the fibrinogen agent is full-length fibrinogen.

10. The non-human animal model of claim 1, wherein the fibrinogen agent is a biologically active fragment of fibrinogen.

11. The non-human animal model of claim 1, wherein the fibrinogen agent is labeled.

12. A non-human animal model of demyelination, wherein said demyelination is induced by the administration of a fibrinogen agent to one or more regions of the animal's central nervous system (CNS), and wherein said fibrinogen agent results in demyelination of neurons in the CNS of the animal.

13. The non-human animal of claim 12, wherein the fibrinogen agent is administered into one or more regions of the brain.

14. The method of claim 13, wherein the region of interest is the dentate gyrus, substantia nigra, cortex or corpus callosum.

15. The non-human animal of claim 12, wherein the animal exhibits cognitive impairment resulting from the administration of the fibrinogen agent.

16. The non-human animal of claim 12, wherein the fibrinogen agent is administered to the spinal cord.

17. The non-human animal of claim 12, wherein the induced neuronal injury is localized neuronal injury.

18. The non-human animal of claim 12, wherein the animal model further comprises one or more genetic traits associated with an increased risk of neurodegenerative disease.

19. The non-human animal model of claim 12, wherein the fibrinogen agent is full-length fibrinogen.

20. The non-human animal model of claim 12, wherein the fibrinogen agent is a biologically active fragment of fibrinogen.

21. The non-human animal model of claim 12, wherein the fibrinogen agent is labeled.

* * * * *